US007381585B2

(12) United States Patent
Afzali-Ardakani et al.

(10) Patent No.: US 7,381,585 B2
(45) Date of Patent: Jun. 3, 2008

(54) HETERO DIELS-ALDER ADDUCTS OF PENTACENE AS SOLUBLE PRECURSORS OF PENTACENE

(75) Inventors: Ali Afzali-Ardakani, Yorktown Heights, NY (US); Tricia L Breen, Hopewell Junction, NY (US); Christos D Dimitrakopoulos, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 99 days.

(21) Appl. No.: 11/526,943

(22) Filed: Sep. 26, 2006

(65) Prior Publication Data

US 2007/0027317 A1 Feb. 1, 2007

Related U.S. Application Data

(62) Division of application No. 10/300,645, filed on Nov. 20, 2002, now Pat. No. 7,125,989.

(60) Provisional application No. 60/333,312, filed on Nov. 26, 2001.

(51) Int. Cl.
*H01L 51/40* (2006.01)

(52) U.S. Cl. ......... 438/99; 257/E51.001; 257/E51.028; 427/384

(58) Field of Classification Search ........ 257/E51.001, 257/E51.027, E51.028
See application file for complete search history.

(56) References Cited

U.S. PATENT DOCUMENTS 5,946,551 A * 8/1999 Dimitrakopoulos et al. .. 438/99

OTHER PUBLICATIONS

Vogt et al., "Developments and Applications of Amino Derived Chiral Acylnitroso Hetero Diles-Alder Reactions," Tetrahedron Report No. 439, pp. 1317-1348, Apr. 18, 1997.

Bao et al., "Soluble and Processable Regioregular Poly(3-Hexylthiophene) for Thin Film Field-Effect Transistor Applications with High Mobility," American Institute of Physics, pp. 4108-4110, 1996.

Bao et al., "Organic Field-Effect Transistors with High Mobility Based on Copper Phthalocyanine," American Institute of Physics, pp. 3066-3068, 1996.

Herwig et al., "a Soluble Pentacene Precursor: Synthesis, Solid-State Conversion into Pentacene and Application in a Field-Effect Transistor," Advanced Matter, vol. 11, No. 3, pp. 480-483, 1999.

Dimitrakopoulos et al., "Molecular Beam Deposited Thin Films of Pentacene for Organic Field Effect Transistor Applications," American Institute of Physics, pp. 2501-2508, 1996.

Freer et al., "Generation of a Thioaldehyde S-Oxide (Suphine) by retro-Diels-Alder Reactions," J. Chem. Soc., Chem. Commun., 1987.

(Continued)

*Primary Examiner*—Stephen W. Smoot
(74) *Attorney, Agent, or Firm*—Ohlandt, Greeley, Ruggiero & Perle, L.L.P.; Daniel P. Morris, Esq.

(57) ABSTRACT

The present invention describes organic solvent-soluble Diels-Alder adducts of polycyclic aromatic compounds, such as, oligothiophene, perylene, benzo[ghi]perylene, coronene and polyacenes, with variety of dienophiles containing at least one heteroatom and in some cases two heteroatoms bonded to aromatic moiety, such as, thioxomalonates, azodicarboxylates, thialdehyde, acylnitroso and N-sulfinylamides. The Diels-Alder adducts are prepared by a simple, one step cycloaddition reaction of the polycyclic aromatic compounds, such as, pentacene, or other fused aromatic compounds, with heterodienophiles. The Diels-Alder adducts according to the present invention all form soluble adducts with pentacene and can be converted back to pentacene by retro-Diels-Alder reaction at moderate (60-250° C.) temperatures both in bulk, in solution or as thin-films.

28 Claims, 3 Drawing Sheets

OTHER PUBLICATIONS

Blandon et al., "*Ethyl and Methyl Thioxoacetates, Dienophilic Thioaldehydes Formed from sulphenyl Chlorides by 1,2-Elimination*," J. Chem. Soc. Perkin Trans. I, pp. 1541-1545, 1985.

Kirby et al., "*The Transient Dienophile Diethyl Thioxomalonate and its S-Oxide (sulphine) Formed by Retro-Diels-Alder Cleavage Reactions*," J. Chem. Soc. Perkin Trans. I, pp. 3176-3181, 1990.

Garnier et al., "*Structural Basis for High Carrier Mobility in Conjugated Oligomers*," Elservier Sequoia, Lausanne, pp. 163-171, 1991.

Klauk et al., "*Pentacene Oganic Thin-Film Transistors and ICs*," Deposition, pp. 63-64, 66-67 Mar. 2000.

Prabhakaran et al., Synlett, vol. 5, pp. 658-662, 2000.

\* cited by examiner

HETERO DIELS-ALDER ADDUCTS OF PENTACENE AS SOLUBLE PRECURSORS OF PENTACENE

BACKGROUND OF THE INVENTION

This application claims priority from Provisional Application Ser. No. 60/333,312 filed on Nov. 26, 2001. This application is a Divisional of and claims priority from U.S. application Ser. No. 10/300,645 filed on Nov. 20, 2002 now U.S. Pat. No. 7,125,989.

FIELD OF INVENTION

This invention relates to the synthesis of various Diels-Alder adducts of polycyclic aromatic compounds, such as, pentacene, with heterodienophiles having at least one hetero atom from N, O, or sulfur. The adducts are highly soluble in common organic solvents and can be easily converted back to pentacene in solid state by heating at moderate temperatures.

BACKGROUND OF THE INVENTION

Thin-film transistors and other electronic devices using organic semiconductors are emerging as alternatives to established methods using amorphous silicon ($\alpha$-Si:H) as the semiconductor.

A variety of organic compounds have been proposed and tested as semiconducting materials for TFT devices. For example, among the p-channel (hole transport) materials that have been characterized are thiophene oligomers proposed as organic semiconductor material for TFT in Garnier, F., et al., "Structural basis for high carrier mobility in conjugated oligomers" Synth. Meth., Vol. 45, p. 163 (1991), and phthalocyanines described in Bao, Z., et al., "Organic Filed-effect transistors with high mobility based on copper phthalocyanine" Appl. Phys. Lett., Vol. 69, p. 3066 (1996). Pentacene, which is a member of poly(acene) compounds has been proposed as an organic semiconductor material in Lin et al. IEEE 54th Annual Device Research Conference, 1996, pages 2136-2139, and Dimitrakopoulos et al., J. Appl. Phys., 80 (4), 1996, pages 2501-2507.

Some soluble organic compounds have also been characterized as organic semiconducting materials. For example poly(3-alkylthiophene) described in Bao, Z., et al., "Soluble and Processable regioregular poly(3-hexylthiophene) for thin film field-effect transistors application with high mobility" Appl. Phys. Lett., Vol. 69, page 4108 (1996).

An attractive material would have a high carrier mobility which is close to that of amorphous silicon (0.1-1 $cm^2.V^{-1}.Sec^{-1}$), with a very high on/off ratio (>$10^5$). For an organic material to replace amorphous silicon, not only would it have the electrical properties cited above but also it should be processable from solution so that it could become commercially attractive.

Among the organic compounds which have been studied as semiconductors, only regioregular poly(3-hexylthiophene) is readily soluble in organic solvents and thin films of this compound has been processed from solution for construction of TFTs. The drawback for this compound is that it has relatively low ($5 \times 10^{-2}$ $cm^2.V^{-1}.Sec^{-1}$) carrier mobility and even much less satisfactory on/off ratio of less than 100. In addition, because thin films of this polymer are not stable in air and its field-effect characteristics deteriorates on exposure to air, its application as semiconductor becomes less desirable.

The best performance as semiconductor among organic materials to date has been achieved by thin films of pentacene deposited under high vacuum and temperature as reported by Dimitrakopoulos et al., in U.S. Pat. Nos. 5,946,511; 5,981,970 and 6,207,472 and other publications by Brown et al., J. Appl. Phys. 80(4), 1996, pages 2136-2139 and Dimitrakopoulos et al., J. Appl. Phys. 80 (4), pages 2501-2507.

Recently, thin-film transistors on plastic substrates using evaporated films of pentacene as the p-channel carrier with mobility of 1.7 $cm^2.V^{-1}.Sec.^{-1}$ and an on/off ratio of $10^8$ has been reported by Jakson et al., in Solid State Technology, Vol. 43 (3), 2000, pages 63-77.

Thin films of pentacene are very stable in air and even moderate temperatures and as far as performance is concerned, pentacene is the most attractive organic material to replace amorphous silicon.

The drawback for pentacene is that it is insoluble in common organic solvents and it can only be deposited as thin film by expensive high vacuum and temperature techniques.

There has been very little effort for the synthesis of soluble pentacene derivatives and the only example of soluble pentacene is by Muellen, K. et al., "A soluble pentacene precursor: Synthesis, solid-state conversion into pentacene and application in a field-effect transistor," Adv. Mat. 11(6), p. 480 (1999), in which a precursor of pentacene is synthesized by a tedious multi-step synthetic approach. The derivative, which is soluble in organic compounds and can be processed from solution, is converted back to pentacene by heating at moderate to high temperature (140-200° C.).

The drawback for using this compound as a pentacene precursor is that due to multi-step synthesis (more than 9 steps), its preparation, especially in large scale is almost impractical. In addition, its conversion to pentacene occurs at a relatively high temperature, which prevents the use of most plastics as substrates.

Thioaldehydes, RCHS, and the more stable thioxoacetate ROCO—CHS have been used in Diels-Alder reactions with variety of dienes as reported by G. Kirby et al., in "Ethyl and methyl thioxoacetates, dienophilic thioaldehydes formed from sulphenyl chlorides by 1,2-elemination," J. Chem. Soc., Perkin Trans, 1, 1541 (1985).

The adduct of anthracene which is the second member of polyacene with thioxoacetate and its oxidation to less stable S-oxide was reported by G. Kirby et al. in "Generation of a thioaldeyde S-oxide by retro-Diels-Alder reaction", Chem. Commun., 718, 1987. This reaction, shown below, is an example of a Diels-Alder adduct as a precursor of fused aromatic compounds.

Another example of hetero dienophile with one hetero atom are oxomalonates and thioxomalonates (RR'C=O and RR'C=S respectively) as shown by J. Barluenga et al., in "Diels-Alder reaction of unactivated 2-Aza-1,3-dienes with diethyl ketomalonate: A carbon dioxide equivalent" Tetrahedron Lett., Vol. 30, pages 2685-2688, 1989 and G. Kirby et al., in "The transient dienophile and its S-oxide (sulphine) formed by retro Diels-Alder reaction", J. Chem. Soc., Perkin Trans., 3175, 1990 for oxo- and thioxomalonate respectively. Again, one of the dienes shown to react with this hetero dienophile, is anthracene in which a labile anthracene adduct having carbon-sulfur bond is formed as shown in the following scheme:

Hetero Diels-Alder reactions with dienolphiles having two active heteroatoms have also been used successfully for the preparation of a variety of nitrogen and/or sulfur containing compounds. An example of such dienophiles are acyinitroso (RCO—N=O) compounds which are generated in situ from corresponding hydroxamic acids. An extensive review of Diels-Alder reactions of various dienes with acylnitroso dienophiles has been published by M. Miller et al., in "Development and applications of amino acid derived chiral acyinitroso hetero Diels-Alder reaction", Tetrahedron, Vol. 54, pages 1317-1348, 1998. Again, the use of anthracene or its derivatives has been a prime example in this report as shown in the following scheme:

Other hetero dienophiles with two heteroatoms which have been used in Diels-Alder reactions are those with —N=N— and R—N=S=O functionalities. Examples of dienophiles with nitrogen-nitrogen double bonds are various azodicarboxylates (ROCO—N=N—COOR) and those with nitrogen-sulfur double bonds are N-sulfinyl amines or N-sulfinyl amides (R—N=S=O) or (RCO—N=S=O).

None of the above references describes precursors of polycyclic aromatic compounds that are: (1) Diels-Alder adducts of a polycyclic aromatic compound, such as, pentacene, with a dienophile and (2) highly soluble in common organic solvents.

Accordingly, it is an object of this invention to synthesize precursors of polycyclic aromatic compounds, such as, pentacene, which are highly soluble in common organic solvents.

Another object of this invention is to provide a precursor of a polycyclic aromatic compound, such as, pentacene, that is convertible in bulk or as thin films back to pentacene in a retro-Diels-Alder reaction at relatively low temperatures.

Still another object of the invention is to devise a simple synthetic approach to the preparation of these compounds, which produces high yields of the compounds and is easily scalable.

Still another object of this invention is to cast thin films of these materials from solution and regenerate thin films of pentacene upon heating the former at low or moderate temperatures.

The present invention provides highly soluble precursors of polycyclic aromatic compounds, such as, pentacene, which are synthesized in one step via the Diels-Alder reaction of polycyclic aromatic compound with a variety of dienophiles having at least one heteroatom in the dienophile moiety.

SUMMARY OF THE INVENTION

The present invention provides a Diels-Alder adduct of a polycyclic aromatic compound with a dienophile, wherein the polycyclic aromatic compound is selected from: oligothiophene, perylene, benzo[ghi]perylene, coronene and polyacene; and wherein the dienophile is represented by the formula:

$R^1—X=Y—R^2$ wherein each X and Y can independently be N or $CR^7$;
wherein $R^1—X=$ can be O, S, SO and $SO_2$; and
wherein each $R^1$, $R^2$ and $R^7$ can independently be hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —NO$_2$, —CO$_2$R, —PO$_3$H, —SO$_3$H, trialkylsilyl and acyl; wherein the acyl is represented by the formula: R$^8$CO— wherein R$^8$ can be hydrogen, alkyl of 1-12 carbon atoms, aryl, substituted aryl, aralkyl and fluoroalkyl;

with the proviso that at least one of X and Y is a hetero atom selected from: N, O and S.

The present invention further provides a process for preparing a Diels-Alder adduct of a polycyclic aromatic compound with a dienophile, the process comprising the step of contacting:

(a) a polycyclic aromatic compound selected from: oligothiophene, perylene, benzo[ghi]perylene, coronene and a compound represented by the formula:

wherein each R$^3$, R$^4$, R$^5$ and R$^6$ is independently selected from: hydrogen, alkyl of 1-12 carbon atoms, aryl, substituted aryl, a group wherein R$^3$ and R$^4$ together form one or more fused benzo rings and a group wherein R$^5$ and R$^6$ together form one or more fused benzo rings, wherein n is at least 1; and (b) dienophile represented by the formula:

R$^1$—X=Y—R$^2$ wherein each X and Y is independently selected from: N and CR$^7$; wherein R$^1$—X= can be O, S, SO and SO$_2$; wherein each R$^1$, R$^2$ and R$^7$ is independently selected from: hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —NO$_2$, —CO$_2$R, —PO$_3$H, —SO$_3$H, trialkylsilyl and acyl; wherein the acyl is represented by the formula: R$^8$CO— wherein R$^8$ can be hydrogen, alkyl of 1-12 carbon atoms, aryl, substituted aryl, aralkyl and fluoroalkyl; with the proviso that at least one of X and Y is a hetero atom selected from: N, O and S;

wherein the contacting is carried out under reaction conditions sufficient to produce the Diels-Alder adduct.

The present invention further still provides a method forming a thin film of a Diels-Alder adduct of a polycyclic aromatic compound with a dienophile, the method comprising the steps of:

(a) applying onto a substrate a solution of a Diels-Alder adduct of a polycyclic aromatic compound with a dienophile in a suitable solvent, wherein the polycyclic aromatic compound is selected from: oligothiophene, perylene, benzo[ghi]perylene, coronene and a compound represented by the formula:

wherein each R$^3$, R$^4$, R$^5$ and R$^6$ is independently selected from: hydrogen, alkyl of 1-12 carbon atoms, aryl, substituted aryl, a group wherein R$^3$ and R$^4$ together form one or more fused benzo rings and a group wherein R$^5$ and R$^6$ together form one or more fused benzo rings, wherein n is at least 1; and wherein the dienophile is represented by the formula:

R$^1$—X=Y—R$^2$ wherein each X and Y is independently selected from: N and CR$^7$; wherein R$^1$—X= can be O, S, SO and SO$_2$; and wherein each R$^1$, R$^2$ and R$^7$ is independently selected from: hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —NO$_2$, —CO$_2$R, —PO$_3$H, —SO$_3$H, trialkylsilyl and acyl; wherein the acyl is represented by the formula: R$^8$CO— wherein R$^8$ can be hydrogen, alkyl of 1-12 carbon atoms, aryl, substituted aryl, aralkyl and fluoroalkyl; with the proviso that at least one of X and Y is a hetero atom selected from: N, O and S; and

(b) evaporating the solvent to produce the thin film of the Diels-Alder adduct of the polycyclic aromatic compound with the dienophile.

The present invention also provides a method of forming a thin film of polycyclic aromatic compound, comprising the steps of:

(a) applying onto a substrate a solution of a Diels-Alder adduct of a polycyclic aromatic compound with a dienophile in a suitable solvent, wherein the polycyclic aromatic compound is selected from: oligothiophene, perylene, benzo[ghi]perylene, coronene and a compound represented by the formula:

wherein each R$^3$, R$^4$, R$^5$ and R$^6$ is independently selected from: hydrogen, alkyl of 1-12 carbon atoms, aryl, substituted aryl, a group wherein R$^3$ and R$^4$ together form one or more fused benzo rings and a group wherein R$^5$ and R$^6$ together form one or more fused benzo rings, wherein n is at least 1; and wherein the dienophile is represented by the formula:

R$^1$—X=Y—R$^2$ wherein each X and Y is independently selected from: N and CR$^7$; wherein R$^1$—X= can be O, S, SO and SO$_2$; and wherein each R$^1$, R$^2$ and R$^7$ is independently selected from: hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —NO₂, —CO₂R, —PO₃H, —SO₃H, trialkylsilyl and acyl; wherein the acyl is represented by the formula: R⁸CO— wherein R⁸ can be hydrogen, alkyl of 1-12 carbon atoms, aryl, substituted aryl, aralkyl and fluoroalkyl; with the proviso that at least one of X and Y is a hetero atom selected from: N, O and S;

(b) evaporating the solvent to produce the thin film of the Diels-Alder adduct of the polycyclic aromatic compound with the dienophile; and (c) heating the thin film of the Diels-Alder adduct at a temperature and for a period of time sufficient to convert the Diels-Alder adduct back to the polycyclic aromatic compound.

More particularly, the present invention provides a Diels-Alder adduct of a polycyclic aromatic compound with a dienophile represented by the formula:

wherein each X and Y is independently selected from: N and CR⁷;

wherein R¹—X═ can be O, S, SO and SO₂; and wherein each R¹, R² and R⁷ is independently selected from: hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —NO₂, —CO₂R, —PO₃H, —SO₃H, trialkylsilyl and acyl; wherein the acyl is represented by the formula: R⁸CO— wherein R⁸ can be hydrogen, alkyl of 1-12 carbon atoms, aryl, substituted aryl, aralkyl and fluoroalkyl;

with the proviso that at least one of X and Y is a hetero atom selected from: N, O and S.

DETAILED DESCRIPTION OF THE INVENTION

The present invention describes organic solvent-soluble Diels-Alder adducts of polycyclic aromatic compounds, such as, oligothiophene, perylene, benzo[ghi]perylene, coronene, oligothiophene and polyacenes with variety of dienophiles containing at least one heteroatom and in some cases two heteroatoms bonded to aromatic moiety, such as, thioxomalonates, azodicarboxylates, thialdehyde, acylnitroso and N-sulfinylamides.

The Diels-Alder adducts are prepared by a simple, one step cycloaddition reaction of the polycyclic aromatic compounds, such as, pentacene, or other fused aromatic compounds, with heterodienophiles. The Diels-Alder adducts according to the present invention all form soluble adducts with pentacene and can be converted back to pentacene by retro-Diels-Alder reaction at moderate (60-250° C.) temperatures both in bulk, in solution or as thin-films.

Applicants have discovered that Diels-Alder adducts according to the present invention having one to two heteroatoms bonded to aromatic moiety makes such adducts undergo a retro-Diels-Alder reactions at low to moderate temperatures.

Applicants have also discovered that the Diels-Alder reactions with heterodienophiles are catalyzed by variety of Lewis acid catalysts and are carried out at low to moderate temperatures.

Although there has been great body of work on Diels-Alder reactions and adducts of anthracene (structure I, n=1) which is the second member of polyacenes, very little or no work has been reported on Diels-Alder reactions or adducts for higher members of these class of compound like tetracene (n=2) and particulary for pentacene (n=3).

This might be due to the fact that higher members of polyacenes are not soluble in most organic solvents.

The present invention also describes a simple approach in which pentacene (or other polyacenes of I) are treated with a dienophile (formula II) to form a Diels-Alder adduct represented by formula III.

wherein each X and Y is independently selected from: N and CR⁷;

wherein R¹—X═ can be O, S, SO and SO₂; and wherein each R¹, R² and R⁷ is independently selected from: hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —NO₂, —CO₂R, —PO₃H, —SO₃H, trialkylsilyl and acyl; wherein the acyl is represented by the formula: R⁸CO— wherein R⁸ can be hydrogen, alkyl of 1-12 carbon atoms, aryl, substituted aryl, aralkyl and fluoroalkyl;

with the proviso that at least one of X and Y is a hetero atom selected from: N, O and S.

Polyacenes are compounds, which can be represented by the formula:

wherein each $R^3$, $R^4$, $R^5$ and $R^6$ is independently selected from: hydrogen, alkyl of 1-12 carbon atoms, aryl, substituted aryl, a group wherein $R^3$ and $R^4$ together form one or more fused benzo rings and a group wherein $R^5$ and $R^6$ together form one or more fused benzo rings, wherein n is at least 1, and preferably, n is at least 2.

The polyacene can be represented by the formula:

where n is from 2 to 6. In a preferred embodiment, n is equal to 3 such that the polycyclic aromatic compound represented by the above formula represents pentacene. A notable example of the polyacenes is pentacene.

The Diels-Alder reactions can easily be carried out with other members of polyacenes like tetracene and hexacene.

Other fused aromatic compounds like oligothiophene, perylene (III), benzo[g,h]perylene (IV), coronene (V) and other fused aromatic compounds capable of forming Diels-Alder adducts can also be used to prepared soluble precursors of these sparingly soluble compounds.

III

IV

V

-continued

Oligothiophene wherein n is equal or greater than 1, and preferably from 1 to 5; and wherein $R^1$ and $R^2$ are independently selected from the group consisting of hydrogen, alkyl of 1-12 carbon atoms, acyl, alkylphosphonate, hydroxyalkyl, mercaptoalkyl, thiol, carboxylic acid, carboxylic acid ester, trialkoxysilane, amino, alkylamino, dialkylamino and aminoalkane.

The dienophile is represented by the formula:

$$R^1\text{—}X\text{=}Y\text{—}R^2$$

wherein each X and Y is independently selected from: N and $CR^7$;

wherein $R^1$—X= can be O, S, SO and $SO_2$; and wherein each $R^1$, $R^2$ and $R^7$ is independently selected from: hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —$NO_2$, —$CO_2R$, —$PO_3H$, —$SO_3H$, trialkylsilyl and acyl; wherein the acyl is represented by the formula: $R^8CO$— wherein $R^8$ can be hydrogen, alkyl of 1-12 carbon atoms, aryl, substituted aryl, aralkyl and fluoroalkyl;

with the proviso that at least one of X and Y is a hetero atom selected from: N, O and S.

In a preferred embodiment where the polycyclic aromatic compound is a polyacene, the Diels-Alder adduct can be represented by the formula:

wherein each X and Y is independently selected from: N and $CR^7$;

wherein $R^1$—X= can be O, S, SO and $SO_2$; and wherein each $R^1$, $R^2$ and $R^7$ is independently selected from: hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —$NO_2$, —$CO_2R$, —$PO_3H$, —$SO_3H$, trialkylsilyl and acyl; wherein the acyl is represented by the formula: $R^8CO$— wherein $R^8$ can be hydrogen, alkyl of 1-12 carbon atoms, aryl, substituted aryl, aralkyl and fluoroalkyl;

with the proviso that at least one of X and Y is a hetero atom selected from: N, O and S.

The dienophiles described in this invention are chosen from known compounds and all have at least one heteroatom, such as, N, O or S, connected by a double bond to a second heteroatom or carbon.

Examples of the dienophiles which are used in this invention include dialkylazodicarboxylate, thiooxomalonates, N-sulfinylamides, acylnitroso compounds and other compounds that fulfill the above requirements.

Diels-Alder reaction of conjugated dienes with ethylenic or acetylenic dienophiles remain one of the most useful transformations in organic synthesis. Heterodienophiles of the type RR'C=X have been employed less frequently but have considerable potential when only one carbon-carbon bond is required in the product.

Because of the high reactivity of these hetero dienophiles and the solubility of dienes used in these examples, the Diels-Alder reactions are mostly carried out at low to room temperatures without the use of any catalyst. In cases where dienes are less reactive and have marginal solubility, like anthracene and its derivatives, the Diels-Alder reaction is carried out at moderate temperatures, usually refluxing in low boiling solvents. But because anthracene and its derivatives are soluble in hot solvents, the reaction can be carried out without the presence of a catalyst.

Higher homologous of polyacene like tetracene and pentacene have little or no solubility in most common organic solvents in which a Diels-Alder reactions is carried out. Because of lack of solubility there has been no report of Diels-Alder reaction of pentacene or tetracene with any dienophiles, and particularly with hetero dienophiles.

In this invention, Diels-Alder reactions and adducts of pentacene with various hetero dienophiles are described. The common feature of all these reactions will be the use of a Lewis acid to promote the reaction at moderate temperature so that the thermally labile adducts can be isolated.

An example of such an adduct wherein the polycyclic aromatic compound is pentacene and the dienophile is a thioxocarboxylate is represented by the formula:

The above Diels-Alder adduct in which the sulfur atom is oxidized to the corresponding sulfoxide is represented by the formula:

wherein R is selected from: hydrogen, alkyl of 1-12 carbon atoms, alkoxy, acyl, aryl, aralkyl, chloroalkyl, fluoroalkyl and substituted aryl having a substituent selected from: —F, —Cl, —Br, —NO$_2$, —CO$_2$R, —PO$_3$H, —SO$_3$H, trialkylsilyl and acyl; wherein said acyl is represented by the formula: R$^8$CO— wherein R$^8$ is selected from: hydrogen, alkyl of 1-12 carbon atoms, aryl, substituted aryl, aralkyl and fluoroalkyl;

Another example is the Diels-Alder reaction of thioxomalonate with pentacene to form an adduct with one carbon-sulfur bond as depicted in the following scheme. Diethyl thioxomalonate is prepared in situ from the reaction of diethyl oxomalonate and phosphorous pentasulfide and reacted with pentacene in the presence of a catalyst or by heating in pyridine.

wherein each R is independently selected from: hydrogen, alkyl of 1-12 carbon atoms, alkoxy, acyl, aryl, aralkyl, chloroalkyl, fluoroalkyl and substituted aryl having a substituent selected from: —F, —Cl, —Br, —NO$_2$, —CO$_2$R, —PO$_3$H, —SO$_3$H, trialkylsilyl and acyl; wherein said acyl is represented by the formula: R$^8$CO— wherein R$^8$ is selected from: hydrogen, alkyl of 1-12 carbon atoms, aryl, substituted aryl, aralkyl and fluoroalkyl;

At temperatures higher than 150° C., the thioxomalonate adduct, which is isolated by column chromatography as a white crystalline compound, undergoes a retro Diels-Alder reaction to pentacene. However, if the sulfide is oxidized to corresponding S-oxide, then the adduct can be converted back to pentacene at temperature as low as 150° C.

Both the sulfide and S-oxide adduct are highly soluble in common organic solvents and can be processed from solution to form thin films on substrates.

Another class of adducts of pentacene is Diels-Alder reaction products of pentacene and dialkyl or diaralkylazodicarboxylates. These compounds are by themselves thermally labile and decompose above 100° C. Therefore, any Diels-Alder reaction of these compounds with pentacene has to be carried out low to moderate temperature.

The Diels-Alder adduct where the dienophile is an azodicarboxylate of the formula RO—CO—N=N—COOR is shown below:

R can be alkyl of 1-12 carbon atoms, aryl, aralkyl, chloroalkyl, fluoroalkyl and substituted aryl having a substituent selected from: —F, —Cl, —Br, —NO$_2$, —CO$_2$R, trialkylsilyl and acyl; wherein the acyl is represented by the formula: R$^8$CO— wherein R$^8$ can be hydrogen, alkyl of 1-12 carbon atoms, aryl, substituted aryl, aralkyl, chloroalkyl and fluoroalkyl.

Preferably, R is benzyl, alkyl of one to five carbon atoms, partially or fully chlorinated alkyl of one to four carbon atoms and partially or fully fluorinated alkyl of one to four carbon atoms.

The above Diels-Alder can be hydrolyzed to form a cyclic diamine compound represented by the formula:

and the diamine can be oxidized to give an azo compound represented by the formula:

Employing a Lewis acid catalyst, such as, titanium tetrachloride facilitates the Diels Alder reaction so it can be carried out at temperature below −40° C. Alternatively, less active catalysts like silver tetrafluoroborate or methyl rhenium trioxide can be used to run the reaction above room temperature by refluxing the mixture of pentacene, diazodicarboxylate and the catalyst in a low boiling solvent like THF or chloroform.

These diaza adducts of pentacene are stable to high temperatures and as such are not good candidates as pentacene precursors because thin films of these compounds have to be heated above 280° C. to convert to pentacene. For example, the adduct of diethyl diazodicarboxylate (R=ethyl) has a melting point of 257° C. and is stable up to 300° C. But when the carboxylate groups are hydrolyzed to the corresponding acid, which automatically undergo decarboxylation to form the cyclic diamine, or oxidized form of the latter to diazo derivative, then the adduct becomes highly unstable and can be converted back to pentacene at moderate temperatures (50-100° C.). Thus, an important step in this process is the removal of the carboxylate protecting group at low temperatures so as to be able to isolate the amine or diazo compounds.

The adducts of pentacene with a variety of dialkyl azodicarboxylate were prepared. It was found that bis-trichloroethyl carboxylates (R=CCl$_3$—CH$_2$—) can easily be removed at room temperature in THF by treatment with zinc powder to give the corresponding diamine.

In yet another example of Diels-Alder reaction of pentacene with hetero dienophiles, N-Sulfinyl acetamide (R=CH$_3$CO—) and N-sulfinyl benzyl carbamate (R=C$_6$H$_5$CH$_2$OCO—) were prepared and reacted with pentacene in the presence of methyl rhenium trioxide as Lewis acid catalyst. In both cases, high yields of the adduct were obtained and the compounds found to be highly soluble in many organic solvents.

Figure 2:
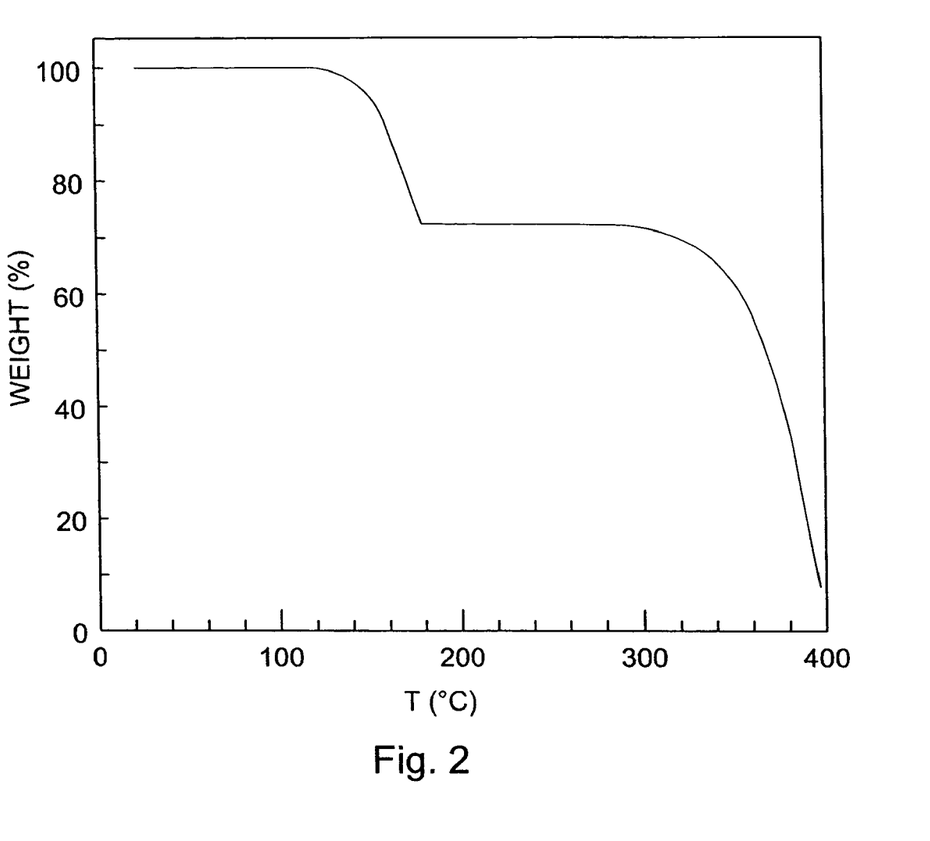
FIG. 2 shows thermogravimetric analysis (TGA) diagram of pentacene-N-sulfinyl acetamide adduct.
Figure 3:
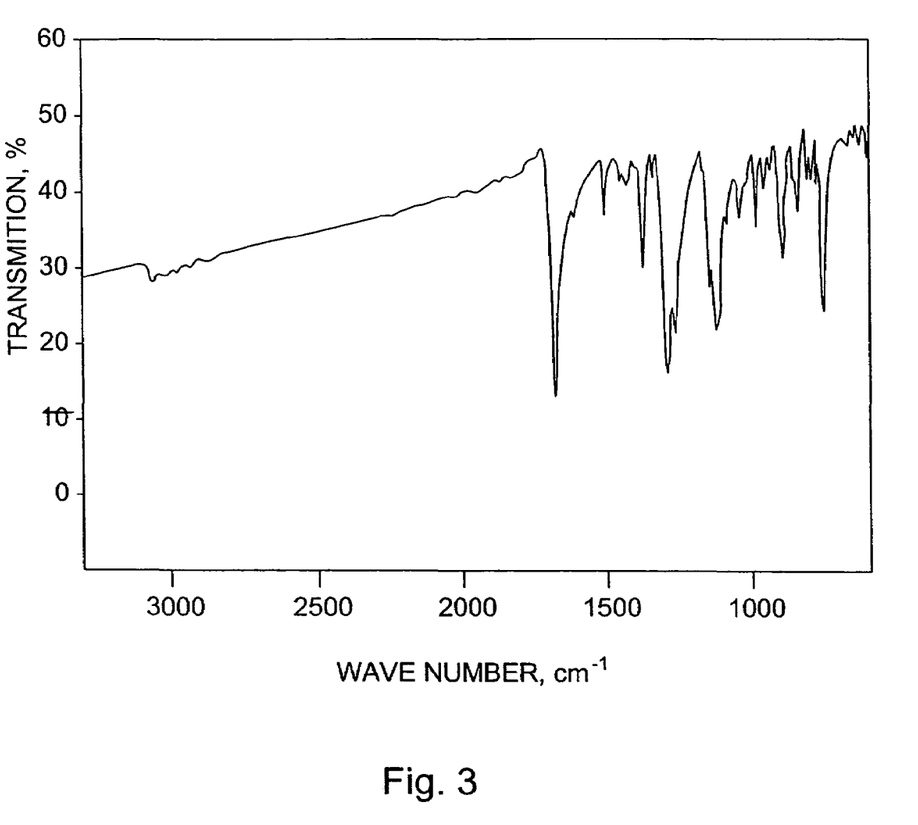
FIG. 3 shows the IR spectrum of pentacene-N-sulfinyl acetamide adduct.

Thin films of these compounds were cast from solution and then heated at 120-140° C. to transform the compounds back to pentacene is confirmed by its UV/VIS spectra (FIG. 1) and thermogravimetric analysis TGA (FIG. 2) and IR spectrum (FIG. 3). Although the onset of the retro Diels-Alder reaction temperature for bulk, as evident from TGA, is about 140° C., thin films of these compounds can be converted back to pentacene at even lower temperatures of 110-120° C.

In still another example of Diels-Alder reaction of pentacene with hetero dienophiles, a Diels-Alder adduct wherein the dienophile is an N-sulfinyl amide compound is represented by the formula:

RCO—N=S=O and the adduct is represented by the formula:

wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —NO$_2$, —CO$_2$R, —PO$_3$H, —SO$_3$H, trialkylsilyl and acyl; wherein the acyl is represented by the formula: R$^8$CO— wherein R$^8$ can be hydrogen, alkyl of 1-12 carbon atoms, aryl, substituted aryl, aralkyl and fluoroalkyl.

Figure 1:
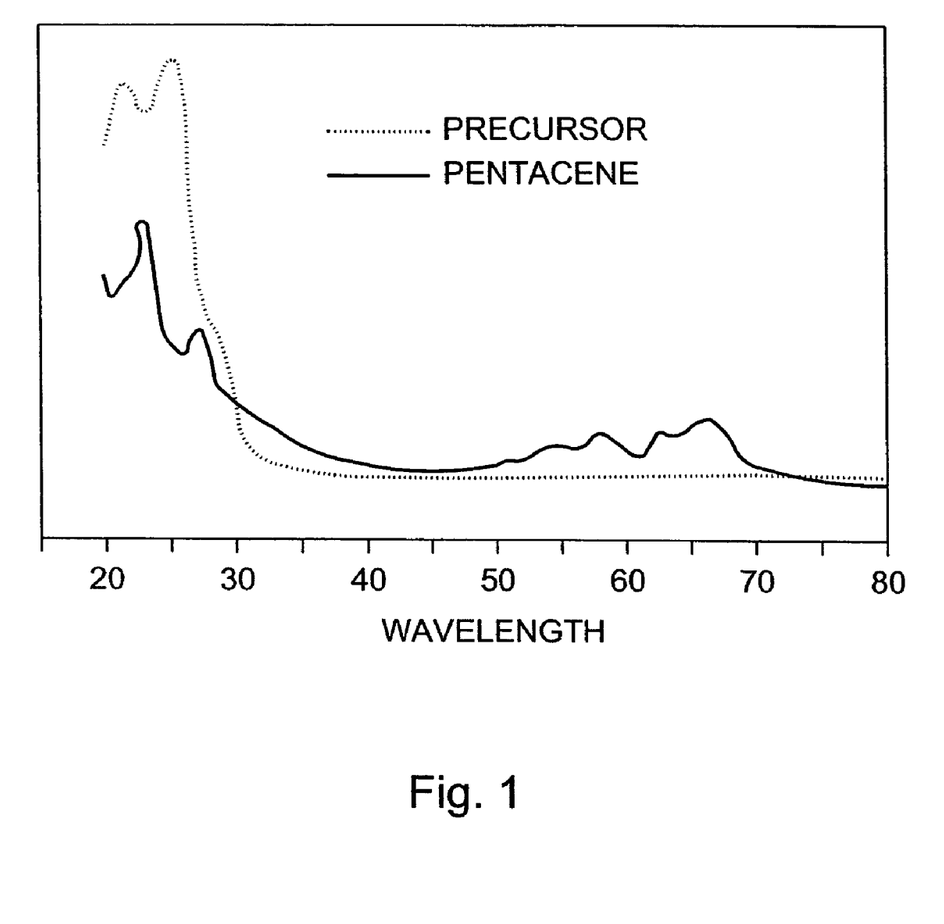
FIG. 1 shows the UV/VIS spectra of Diels-Alder adduct of pentacene and N-sulfinyl acetamide, (a) before and (b) after heating to 130° C., which converts the Diels-Alder adduct back to pentacene.

Referring to FIG. 1, the UV/VIS spectra of Diels-Alder adduct of pentacene and N-sulfinyl acetamide, (a) before and (b) after heating to 130° C., which converts the Diels-Alder adduct back to pentacene is shown.

FIG. 2 shows thermogravimetric analysis (TGA) diagram of pentacene-N-sulfinyl acetamide adduct.

FIG. 3 shows the IR spectrum of pentacene-N-sulfinyl acetamide adduct.

The above Diels-Alder adduct can be hydrolyzed to form a compound represented by the formula:

Although only two examples of N-sulfinyl amides are shown here, N-sulfinyl derivatives are equally attractive candidates for the preparation of soluble pentacene adducts.

For example, N-sulfinyl derivative of fluoroalkylamide like trifluoracetamide (R=CF$_3$—CO—) or higher alkyl amides (R=C$_n$H$_{2n+1}$—CO—, where n=1-10) can be used instead of sulfinyl acetamide. N-Sulfinyl derivatives of aromatic amines (R=aryl) where R— is simply a phenyl group or substituted (nitro, keto, halo, alkyl, fluoroalkyl etc) are known to undergo Diels-Alder reactions and can be used to prepare soluble adducts with pentacene.

R = CH$_3$CO-
C$_6$H$_5$CH$_2$OCO-

In another example of the Diels-Alder reaction of pentacene with a hetero dienophile, a Diels-Alder adduct wherein the dienophile is a nitroso compound is represented by the formula:

wherein R can be hydrogen, alkyl of 1-12 carbon atoms, alkoxy, acyl, aryl, aralkyl, chloroalkyl, fluoroalkyl, substituted aryl having a substituent selected from: —F, —Cl, —Br, —NO$_2$, —CO$_2$R, —PO$_3$H, —SO$_3$H, trialkylsilyl and acyl; wherein the acyl is represented by the formula: R$^8$CO— wherein R$^8$ can be hydrogen, alkyl of 1-12 carbon atoms, aryl, substituted aryl, aralkyl and fluoroalkyl.

Other acylnitroso compounds of general formula R—CO—N=O are very attractive and judged by its adduct with anthracene derivative can be converted back to pentacene at moderate temperatures. An example would be the reaction of pentacene with N-oxyacetamide (R=CH$_3$—) which can be generated from acetylhydroxamic acid and reacted with pentacene in the presence of methyl rhenium trioxide to give desired adduct as shown bellow.

R = C$_n$H$_{2n+1}$,

In the above reaction R— can be chosen from alkyl groups of having one to twelve carbon atoms, halogenated alkyl groups like CF$_3$—(CF$_2$)$_n$— where n is from zero to 10. R could be also an aryl group like phenyl or substituted phenyl with substituents like one or more halogens (Cl, F and Br), nitro group, carboxylic acid or esters, amines or amides, phosphonic acid or ester, trialkyl or trialkoxysilane.

The adducts in which nitrogen is connected to an acyl (RCO) group could further be hydrolyzed to corresponding —NH group by treatment with base as shown in the following reaction.

Thin films of these adducts are prepared from solution by different techniques, e.g., spin-coating, casting, doctor blading, etc. Once thin films of these adducts on substrates are formed, they can easily be converted back to pentacene by heating the substrate on a hot plate or in an oven at modest temperatures. Any residual compounds other than pentacene formed during retro Diels-Alder reaction can be removed by dipping the substrate solvents like alcohols, ethers, ketones and the like, to get pure pentacene films.

In the examples listed above the diene which was employed in Diels-Alder reactions has been pentacene, but other members of polyacenes like tetracene, hexacene and heptacene (structure I, n=2, 4 and 5 respectively) can also be used to make soluble derivatives with hetero dienophiles.

Although in all the structures depicted so far, the dienophile has attached to the middle ring of pentacene (or polyacene in general) it is possible to have the dienophile react with other ring in polycyclic aromatic compounds like pentacene, as depicted in the following structure with R¹—X=Y—R² representing hetero dienophiles of this invention:

wherein each X and Y is independently selected from: N and $CR^7$;

wherein $R^1$—X= can be O, S, SO and $SO_2$; and wherein each $R^1$, $R^2$ and $R^7$ is independently selected from: hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —$NO_2$, —$CO_2R$, —$PO_3H$, —$SO_3H$, trialkylsilyl and acyl; wherein the acyl is represented by the formula: $R^8CO$— wherein $R^8$ can be hydrogen, alkyl of 1-12 carbon atoms, aryl, substituted aryl, aralkyl and fluoroalkyl;

with the proviso that at least one of X and Y is a hetero atom selected from: N, O and S.

The Diels-Alder adducts can be prepared by a process comprising the step of:

contacting:

(a) a polycyclic aromatic compound selected from: oligothiophene, perylene, benzo[ghi]perylene, coronene and a compound represented by the formula:

wherein each $R^3$, $R^4$, $R^5$ and $R^6$ is independently selected from: hydrogen, alkyl of 1-12 carbon atoms, aryl, substituted aryl, a group wherein $R^3$ and $R^4$ together form one or more fused benzo rings and a group wherein $R^5$ and $R^6$ together form one or more fused benzo rings, wherein n is at least 1; and (b) dienophile represented by the formula:

wherein each X and Y is independently selected from: N and $CR^7$; wherein $R^1$—X= can be O, S, SO and $SO_2$; wherein each $R^1$, $R^2$ and $R^7$ is independently selected from: hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —$NO_2$, —$CO_2R$, —$PO_3H$, —$SO_3H$, trialkylsilyl and acyl; wherein the acyl is represented by the formula: $R^8CO$— wherein $R^8$ can be hydrogen, alkyl of 1-12 carbon atoms, aryl, substituted aryl, aralkyl and fluoroalkyl; with the proviso that at least one of X and Y is a hetero atom selected from: N, O and S;

wherein the contacting is carried out under reaction conditions sufficient to produce the Diels-Alder adduct.

The Diels-Alder reaction of hetero dienophiles with polyacenes and other fused aromatic compounds according to the present invention are Lewis acid-catalyzed. The Diels-Alder reaction is carried out at low to moderate temperatures, as the case may be, resulting in the formation of the adducts. Preferably, the Diels-Alder reaction is carried out in the presence of a Lewis acids and protic acids, including compounds, such as, titanium(IV)tetrachloride, tin(IV)tetrachloride, silver tetrafluoroborate, methyl rhenium trioxide, aluminum chloride, diethyl aluminum chloride, silver trifluoroacetate, palladium compounds, sulfuric acid, trifluoroacetic acid, methanesulfonic acid, trifluoromethanesulfonic acid, and many others Lewis and protic acids known in the art.

The reactions are carried out in the presence of a Lewis acid catalyst to lower the transition state energy of the reaction and to be able to run the reaction at temperatures from below zero to moderate temperatures where the adducts are stable.

Depending on the nature of the dienophile and Lewis acid, Diels-Alder reactions can be carried out at very low temperatures (−70° C. to −40° C.) or room temperature or in refluxing low boiling solvents like THF, acetonitrile or chloroform. Diels-Alder reactions of this invention proceeds to give adducts in high yield and the isolation and purification steps are simple. For this reason, the reaction can easily be scaled up for large-scale preparation of the adducts. The products, which are formed in more than 90% yield, can be separated by evaporation of the solvents at reduced pressure and purified by flash chromatography.

The adducts according to the present invention are soluble in variety of common organic solvents including hydrocarbons, chlorinated hydrocarbons, ethers, esters and ketones. This property of the adducts affords the preparation of thin films of the adduct. Accordingly, the present invention includes a method of forming a thin film of a Diels-Alder adduct of a polycyclic aromatic compound with a dienophile, the method comprising the steps of:

(a) applying onto a substrate a solution of a Diels-Alder adduct of a polycyclic aromatic compound with a dienophile in a suitable solvent, wherein the polycyclic aromatic compound is selected from: oligothiophene, perylene, benzo[ghi]perylene, coronene and a compound represented by the formula:

wherein each $R^3$, $R^4$, $R^5$ and $R^6$ is independently selected from: hydrogen, alkyl of 1-12 carbon atoms, aryl, substituted aryl, a group wherein $R^3$ and $R^4$ together form one or more fused benzo rings and a group wherein $R^5$ and $R^6$ together form one or more fused benzo rings, wherein n is at least 1; and wherein the dienophile is represented by the formula:

wherein each X and Y is independently selected from: N and $CR^7$; wherein $R^1$—X= can be O, S, SO and $SO_2$; and wherein each $R^1$, $R^2$ and $R^7$ is independently selected from: hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —NO$_2$, —CO$_2$R, —PO$_3$H, —SO$_3$H, trialkylsilyl and acyl; wherein the acyl is represented by the formula: R$^8$CO— wherein R$^8$ can be hydrogen, alkyl of 1-12 carbon atoms, aryl, substituted aryl, aralkyl and fluoroalkyl; with the proviso that at least one of X and Y is a hetero atom selected from: N, O and S; and

(b) evaporating the solvent to produce the thin film of the Diels-Alder adduct of the polycyclic aromatic compound with the dienophile.

The present invention further includes a method of forming a thin film of a polycyclic aromatic compound itself. The method comprises the steps of:

(a) applying onto a substrate a solution of a Diels-Alder adduct of a polycyclic aromatic compound with a dienophile in a suitable solvent, wherein the polycyclic aromatic compound is selected from: oligothiophene, perylene, benzo [ghi]perylene, coronene and a compound represented by the formula:

wherein each R$^3$, R$^4$, R$^5$ and R$^6$ is independently selected from: hydrogen, alkyl of 1-12 carbon atoms, aryl, substituted aryl, a group wherein R$^3$ and R$^4$ together form one or more fused benzo rings and a group wherein R$^5$ and R$^6$ together form one or more fused benzo rings, wherein n is at least 1; and wherein the dienophile is represented by the formula:

wherein each X and Y is independently selected from: N and CR$^7$; wherein R$^1$—X= can be O, S, SO and SO$_2$; and wherein each R$^1$, R$^2$ and R$^7$ is independently selected from: hydrogen, alkyl of 1-12 carbon atoms, aryl, substituted aryl, aralkyl, alkoxycarbonyl, aryloxycarbonyl, acyl and a group R, wherein R can be hydrogen, alkyl of 1-12 carbon atoms, alkoxy, acyl, aryl, aralkyl, chloroalkyl, fluoroalkyl and substituted aryl having a substituent selected from: —F, —Cl, —Br, —NO$_2$, —CO$_2$R, —PO$_3$H, —SO$_3$H, trialkylsilyl and acyl; wherein the acyl is represented by the formula: R$^8$CO— wherein R$^8$ can be hydrogen, alkyl of 1-12 carbon atoms, aryl, substituted aryl, aralkyl and fluoroalkyl; with the proviso that at least one of X and Y is a hetero atom selected from: N, O and S;

(b) evaporating the solvent to produce the thin film of the Diels-Alder adduct of the polycyclic aromatic compound with the dienophile; and (c) heating the thin film of the Diels-Alder adduct at a temperature and for a period of time sufficient to convert the Diels-Alder adduct back to the polycyclic aromatic compound.

Thin films of these adducts are cast from solution and they can be converted back to pentacene films by simply heating the substrate on which it is coated.

Any suitable substrate can be used to prepare the thin films of the polycyclic aromatic compounds of the present invention as well as the thin films of the Diels-Alder adducts thereof. Preferably, the substrate used to prepare the above thin films is a metal, silicon, plastic, glass or coated glass.

The temperature of the retro-Diels-Alder reaction (conversion of the adducts to pentacene) is dependent on the nature of the dienophile used to prepare the adduct. The conversion can be carried out at temperatures as low as 60° C. in the case of the pentacene diazodicarboxylate adduct after hydrolysis, to more than 180° C. in the case of adduct with thioxomalonate. However, typically, the temperature of heating the thin film of the Diels-Alder adduct is from about 80° C. to about 250° C.

EXPERIMENTAL

EXAMPLE 1

Diels-Alder adduct of pentacene and dimethylazodicarboxylate. Pentacene (834 mg, 3 mmole) and methyl rhenium trioxide (50 mg) were added to a solution of dimethylazodicarboxylate (1.05 g, 6 mmole) in 40 mL of anhydrous chloroform and the solution was refluxed for 18 hours. By this time all the pentacene was dissolved and a yellow clear solution was formed. The solvent was evaporated on rotary evaporator and the residue was flash chromatographed on a column of silica gel first eluting with 9:1 hexane ethyl acetate to remove excess dimethylazodicarboxylate and then elution with 50:50 hexane ethyl acetate gave, after removal of the solvent, the adduct as white powder (1.65 gram, 90% yield), m.p.=273-275° C., onset of decomposition (conversion back to pentacene) at 285° C. IR, KBr: 1754 and 1701 cm$^{-1}$ (carbonyl groups). Exact procedure was followed and adducts of pentacene with diethyl azodicarboxylate (m.p=292-294° C.), dibenzylazodicarboxylate (m.p=295-297° C.) and bis-trichloroethylazodicaboxylate were also synthesized in more than 90% yield.

EXAMPLE 2

Diels-Alder adduct of N-Sulfinyl acetamide and pentacene: Pentacene (556 mg, 2 mmole) was added to a solution of N-sulfinyl acetamide (prepared according to procedure reported by Kin et al., in "New facile synthesis of N-sulfinylamine derivatives using N,N'-sulfinylbisimidazole and N-(chlorosulfinyl)imidazole, Tetrahedron Lett., Vol. 26, 1985, pages 3821-3824) (420 mg, 4 mmole) containing 30 mg. of methyl rhenium trioxide. The mixture was refluxed for 4 hours. The solution was cooled to room temperatures and the solvent was evaporated on rotary evaporator. Excess N-sulfinyl acetamide was removed in high vacuum and the brown solid residue was flash chromatographed on a column of silica gel eluting with 1% methanol in chloroform to give the adduct (690 mg, 91%) as white powder which was crystallized from 2:1 toluene-ethanol. m.p=140-142 (dec.). IR (KBr), 1675, 1376, 1282, 1124 and 893 cm$^{-1}$. Thermogravimetric analysis (FIG. 2), weight loss of 27% starting at 140° C.

Alternative work-up and isolation procedures are also possible, and will be evident to those skilled in the art.

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

We claim:

1. A method of forming a thin film of a Diels-Alder adduct of a polycyclic aromatic compound with a dienophile, said method comprising the steps of:
   (a) applying onto a substrate a solution of a Diels-Alder adduct of a polycyclic aromatic compound with a dienophile in a suitable solvent, wherein said polycyclic aromatic compound is selected from the group consisting of: oligothiophene, perylene, benzo[ghi]perylene, coronene and a compound represented by the formula:

wherein each $R^3$, $R^4$, $R^5$ and $R^6$ is independently selected from the group consisting of: hydrogen, alkyl of 1-12 carbon atoms, aryl, substituted aryl, a group wherein $R^3$ and $R^4$ together form one or more fused benzo rings and a group wherein $R^5$ and $R^6$ together form one or more fused benzo rings, wherein n is at least 1; and
   wherein said dienophile is represented by the formula:

wherein each X and Y is independently selected from the group consisting of: N and $CR^7$; wherein $R^1$—X= together form a group selected from the group consisting of: O, S, SO and $SO_2$; and wherein each $R^1$, $R^2$ and $R^7$ is independently selected from the group consisting of: hydrogen, alkyl of 1-12 carbon atoms, aryl, substituted aryl, aralkyl, alkoxycarbonyl, aryloxycarbonyl, acyl and a group R, wherein R is selected from the group consisting of: hydrogen, alkyl of 1-12 carbon atoms, alkoxy, acyl, aryl, aralkyl, chloroalkyl, fluoroalkyl and substituted aryl having a substituent selected from the group consisting of: —F, —Cl, —Br, —$NO_2$, —$CO_2R$, —$PO_3H$, —$SO_3H$, trialkylsilyl and acyl; wherein said acyl is represented by the formula: $R^8CO$— wherein $R^8$ is selected from the group consisting of: hydrogen, alkyl of 1-12 carbon atoms, aryl, substituted aryl, aralkyl and fluoroalkyl; with the proviso that at least one of X and Y is a hetero atom selected from the group consisting of: N, O and S; and
   (b) evaporating said solvent to produce said thin film of said Diels-Alder adduct of said polycyclic aromatic compound with said dienophile.

2. The method of claim 1, wherein said substrate is selected from the group consisting of: metal, silicon, plastic, glass and coated glass.

3. A thin film of a Diels-Alder adduct of a polycyclic aromatic compound with a dienophile prepared by the method of claim 1.

4. The method of claim 1, wherein n is 2-6.

5. The method of claim 1, wherein n is 2-3.

6. The method of claim 1, wherein n is 1-5.

7. The method of claim 1, wherein said polyacene is represented by the formula:

where n is 2-6.

8. The method of claim 1, wherein n is equal to 3 and said polycyclic aromatic compound is pentacene.

9. The method of claim 1, wherein said dienophile is a thioxocarboxylate compound and said adduct is represented by the formula:

wherein R is selected from the group consisting of: hydrogen, alkyl of 1-12 carbon atoms, alkoxy, acyl, aryl, aralkyl, chloroalkyl, fluoroalkyl and substituted aryl having a substituent selected from the group consisting of: —F, —Cl, —Br, —$NO_2$, —$CO_2R$, —$PO_3H$, —$SO_3H$, trialkylsilyl and acyl; wherein said acyl is represented by the formula: $R^8CO$— wherein $R^8$ is selected from the group consisting of: hydrogen, alkyl of 1-12 carbon atoms, aryl, aralkyl and fluoroalkyl.

10. The method of claim 1, wherein the sulfur atom is oxidized to corresponding sulfoxide and wherein said adduct is represented by the formula:

11. The method of claim 1, wherein said dienophile is thioxomalonate and said adduct is represented by the formula:

wherein R is selected from the group consisting of: hydrogen, alkyl of 1-12 carbon atoms, alkoxy, acyl, aryl, aralkyl, chloroalkyl, fluoroalkyl and substituted aryl having a substituent selected from the group consisting of: —F, —Cl, —Br, —$NO_2$, —$CO_2R$, —$PO_3H$, —$SO_3H$, trialkylsilyl and acyl; wherein said acyl is represented by the formula: $R^8CO$— wherein $R^8$ is selected from the group consisting of: hydrogen, alkyl of 1-12 carbon atoms, aryl, aralkyl and fluoroalkyl.

12. The method of claim 1, wherein said dienophile is a nitroso compound and said adduct is represented by the formula:

wherein R is selected from the group consisting of: hydrogen, alkyl of 1-12 carbon atoms, alkoxy, acyl, aryl, aralkyl, chloroalkyl, fluoroalkyl, substituted aryl having a substituent selected from the group consisting of: —F, —Cl, —Br, —NO$_2$, —CO$_2$R, —PO$_3$H, —SO$_3$H, trialkylsilyl and acyl; wherein said acyl is represented by the formula: R$^8$CO— wherein R$^8$ is selected from the group consisting of: hydrogen, alkyl of 1-12 carbon atoms, aryl, aralkyl and fluoroalkyl.

13. The method of claim 1, wherein said dienophile is an N-sulfinyl amide compound represented by the formula:

RCO—N=S=O wherein said adduct is represented by the formula:

and
wherein R is selected from the group consisting of: hydrogen, alkyl of 1-12 carbon atoms, alkoxy, acyl, aryl, aralkyl, chloroalkyl, fluoroalkyl and substituted aryl having a substituent selected from the group consisting of: —F, —Cl, —Br, —NO$_2$, —CO$_2$R, —PO$_3$H, —SO$_3$H, trialkylsilyl and acyl; wherein said acyl is represented by the formula: R$^8$CO— wherein R$^8$ is selected from the group consisting of: hydrogen, alkyl of 1-12 carbon atoms, aryl, aralkyl and fluoroalkyl.

14. The method of claim 1, wherein said adduct is hydrolyzed to form a compound represented by the formula:

15. The method of claim 1, wherein said dienophile is an azodicarboxylate compound represented by the formula:

RO—CO—N=N—COOR and wherein said adduct is represented by the formula:

and
wherein R is selected from the group consisting of: alkyl of 1-12 carbon atoms, aryl, aralkyl, chloroalkyl, fluoroalkyl and substituted aryl having a substituent selected from the group consisting of: —F, —Cl, —Br, —NO$_2$, —CO$_2$R, trialkylsilyl and acyl; wherein said acyl is represented by the formula: R$^8$CO— wherein R$^8$ is selected from the group consisting of: hydrogen, alkyl of 1-12 carbon atoms, aryl, aralkyl, chloroalkyl and fluoroalkyl.

16. The method of claim 15, wherein R is selected from the group consisting of: benzyl, alkyl of one to five carbon atoms, partially or fully chlorinated alkyl of one to four carbon atoms and partially or fully fluorinated alkyl of one to four carbon atoms.

17. The method of claim 1, wherein said adduct is hydrolyzed to form a cyclic diamine compound represented by the formula:

18. The method of claim 1, wherein said adduct is oxidized to give an azo compound represented by the formula:

19. The method of claim 1, wherein said adduct is represented by the formula:

wherein R is selected from the group consisting of: alkyl of 1-12 carbon atoms, alkoxy, acyl, aralkyl, aryl, and substituted aryl having a substituent selected from the group consisting of: —F, —Cl, —Br, —CO$_2$R, trialkyl- silyl and acyl represented by the formula: $R^8CO$—wherein $R^8$ is selected from the group consisting of: hydrogen, alkyl of 1-12 carbon atoms, aryl, aralkyl and fluoroalkyl; and wherein each $R^3$, $R^4$, $R^5$ and $R^6$ is independently selected from the group consisting of: hydrogen, alkyl of 1-12 carbon atoms and aryl.

20. A method of forming a thin film of polycyclic aromatic compound, comprising the steps of:
   (a) applying onto a substrate a solution of a Diels-Alder adduct of a polycyclic aromatic compound with a dienophile in a suitable solvent, wherein said polycyclic aromatic compound is selected from the group consisting of: oligothiophene, perylene, benzo[ghi]perylene, coronene and a compound represented by the formula:

wherein each $R^3$, $R^4$, $R^5$ and $R^6$ is independently selected from the group consisting of: hydrogen, alkyl of 1-12 carbon atoms, aryl, substituted aryl, a group wherein $R^3$ and $R^4$ together form one or more fused benzo rings and a group wherein $R^5$ and $R^6$ together form one or more fused benzo rings, wherein n is at least 1; and wherein said dienophile is represented by the formula:

wherein each X and Y is independently selected from the group consisting of: N and $CR^7$; wherein $R^1$—X= together form a group selected from the group consisting of: O, S, SO and $SO_2$; and wherein each $R^1$, $R^2$ and $R^7$ is independently selected from the group consisting of: hydrogen, alkyl of 1-12 carbon atoms, aryl, substituted aryl, aralkyl, alkoxycarbonyl, aryloxycarbonyl, acyl and a group R, wherein R is selected from the group consisting of: hydrogen, alkyl of 1-12 carbon atoms, alkoxy, acyl, aryl, aralkyl, chloroalkyl, fluoroalkyl and substituted aryl having a substituent selected from the group consisting of: —F, —Cl, —Br, —$NO_2$, —$CO_2R$, —$PO_3H$, —$SO_3H$, trialkylsilyl and acyl; wherein said acyl is represented by the formula: $R^8CO$— wherein $R^8$ is selected from the group consisting of: hydrogen, alkyl of 1-12 carbon atoms, aryl, substituted aryl, aralkyl and fluoroalkyl; with the proviso that at least one of X and Y is a hetero atom selected from the group consisting of: N, O and S;
   (b) evaporating said solvent to produce said thin film of said Diels-Alder adduct of said polycyclic aromatic compound with said dienophile; and
   (c) heating said thin film of said Diels-Alder adduct at a temperature and for a period of time sufficient to convert said Diels-Alder adduct back to said polycyclic aromatic compound.

21. The method of claim 20, wherein said temperature is from about 80° C. to about 250° C.

22. The method of claim 20, wherein said substrate is selected from the group consisting of: metal, silicon, plastic, glass and coated glass.

23. A thin film of a polycyclic aromatic compound prepared by the method of claim 20.

24. The method of claim 20, wherein n is 2-6.

25. The method of claim 20, wherein n is 2-3.

26. The method of claim 20, wherein n is 1-5.

27. The method of claim 20, wherein said polyacene is represented by the formula:

where n is 2-6.

28. The method of claim 20, wherein n is equal to 3 and said polycyclic aromatic compound is pentacene.

* * * * *